(12) United States Patent
Srinivasa Reddy et al.

(10) Patent No.: US 10,221,122 B2
(45) Date of Patent: Mar. 5, 2019

(54) ENANTIOSPECIFIC PROCESS FOR THE PREPARATION OF (R) AND (S) ENANTIOMERS OF SEX PHEROMONOES OF THE LONG TAILED MEALY BUG

(71) Applicant: Council of Scientific & Industrial Research, New Delhi (IN)

(72) Inventors: Dumbala Srinivasa Reddy, Pune (IN); Remya Ramesh, Pune (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 15/573,291

(22) PCT Filed: May 12, 2016

(86) PCT No.: PCT/IN2016/050136
§ 371 (c)(1),
(2) Date: Nov. 10, 2017

(87) PCT Pub. No.: WO2016/181413
PCT Pub. Date: Nov. 17, 2016

(65) Prior Publication Data
US 2018/0134650 A1 May 17, 2018

(30) Foreign Application Priority Data
May 12, 2015 (IN) .......................... 1323/DEL/2015

(51) Int. Cl.
| | | |
|---|---|---|
| *C07C 67/08* | (2006.01) | |
| *C07C 29/147* | (2006.01) | |
| *C07C 67/03* | (2006.01) | |
| *C07C 67/31* | (2006.01) | |
| *C07C 67/317* | (2006.01) | |
| *C07D 307/935* | (2006.01) | |
| *C07C 33/12* | (2006.01) | |
| *C07C 69/608* | (2006.01) | |
| *C07C 69/732* | (2006.01) | |
| *C07C 69/738* | (2006.01) | |
| *A01N 31/04* | (2006.01) | |
| *A01N 37/06* | (2006.01) | |

(52) U.S. Cl.
CPC .............. *C07C 67/08* (2013.01); *A01N 31/04* (2013.01); *A01N 37/06* (2013.01); *C07C 29/147* (2013.01); *C07C 33/12* (2013.01); *C07C 67/03* (2013.01); *C07C 67/31* (2013.01); *C07C 67/317* (2013.01); *C07C 69/608* (2013.01); *C07C 69/732* (2013.01); *C07C 69/738* (2013.01); *C07D 307/935* (2013.01); *C07B 2200/07* (2013.01); *C07C 2601/08* (2017.05); *C07C 2601/10* (2017.05); *C07C 2602/42* (2017.05)

(58) Field of Classification Search
CPC ..................................................... C07C 67/08
USPC .......................................................... 549/465
See application file for complete search history.

(56) References Cited

PUBLICATIONS

Ramesh, J. Org. Chem. Jul. 8, 2015, 80, 7785-7789.*
Jacobs, J. Org. Chem. 1990, 55, 4051-4062.*
Shunichi Manabe et al., "Sex Pheromonal Activity of (+)—Bornyl Acetate and Related Compounds to the American Cockroach", Journal of Chemical Ecology, vol. 9, No. 3, 1983, pp. 433-448.
Chikao Nishing et al, "Synthesis of Verbenols and Related Alcohols and Their PMR Spectra with Shift Reagent", Agric. Biol. Chem., 43 (9), May 24, 1979, pp. 1967-1974.
Kenji Mori et al. "Useful Reactions in Modem Peromone Synthesis", Current Organic Synthesis, vol. 1, No. 1, 2004, pp. 11-29, Department of Chemistry, Science University of Tokyo, Kagurazaka 1-3, Shinjuku-ku, Tokyo 162-8601, Japan.
C. H. Hassall, "The Baeyer-Villiger Oxidation of Aldehydes and Ketones", University College of the West Indies, Jamaica, pp. 73-106.
Adusumilli Srikrishna et al, "Chemoselective Reductive Deoxygenalton of a, B-Unsaturated Ketones and Allyl Alcohols", Department of Organic Chemistry, Indian Institute of Science, Bangalore—560 012, India, pp. 2347-2350, Tetrahedron Letters, vol. 36. No. 13, Jan. 5. 1995.
E. J. Corey et al, "Pyridinium Chlorochromate, An Efficient Reagent for Oxidation of Primary and Secondary Alcohols to Carbonyl Compounds", Tetrahedron Letters No. 31, pp. 2647-2650, Jun. 10, 1975.

(Continued)

*Primary Examiner* — Nizal S Chandrakumar
(74) *Attorney, Agent, or Firm* — Belles Katz LLC

(57) ABSTRACT

The present invention relates to an enantiospecific process for the preparation of (R) and (S) enantiomers of sex pheromones of the long-tailed mealybug with high enantiopurity.

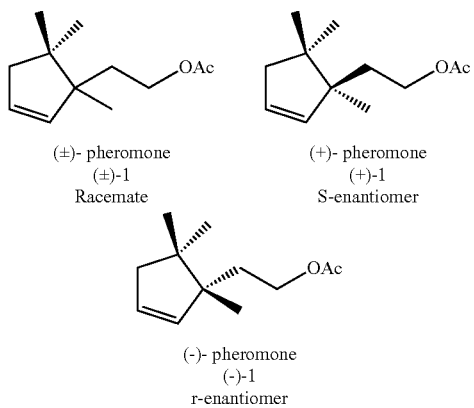

9 Claims, No Drawings

(56) References Cited

PUBLICATIONS

Rafael Gomez-Bombarelli et al, "Mechanisms of Lactone Hydrolysis in Acidic Conditions", The Journal of Organic Chemistry, pp. 6880-6889, pubs.acs.org/joc, 2013.

Andre L. Gemal et al, "Lanthanoids in Organic Sythesis. 6. The Reduction of a-Enones by Sodium Borohydride in the Presence of Lanthanoid Chlorides: Synthetic and Mechanistic Aspects", J. American Chemical Society, vol. 103, No. 18, pp. 5454-5459, 1981.

James L. Fry et al, "Reduction of Ketones to Hydrocarbons with Triethylsilane: m-Nitroethylbenzene", Organic Syntheses, Coll. vol. 7, p. 393(1990); vol. 60, p. 108 (1981), http://www.nap.edu/catalog.php?record_id=12654.

"Only When You Know the Hazards, Can You Take the Necessary Precautionary Measures.", Clip, Chemical Laboratory information Profile, Journal of Chemical Education, vol. 78, No. 9, Sep. 2001, JChemEd.chem.wisc.edu, p. 1176.

Yunfan Zou et al, "Improved Synthesis of the Pheromone of the Longtailed Mealybug", Department of Entomology, University of California, Riverside, CA 92521, pp. 2319-2321, May 14, 2010.

Corresponding International Search Report and Written Opinion for PCT/IN2016/050136 dated Sep. 28, 2016. WO.

Remya Ramesh et al: "Syntheses and Determination of Absolute Configurations and Biological Activities of the Enantiomers of the Longtailed Mealybug Pheromone", The Journal of Organic Chemistry, vol. 78, No. 12, Jun. 21, 2013, pp. 6281-6284, XP055305934, US ISSN: 0022-3263, DOI: 10.1021/jo400491N cited in the application figures 1-2.

Sou Yunfan et al: "Improved synthesis of the pheromone of the long-tailed mealybug", Synlett, Georg Thieme Verlag, DE, No. 15, Aug. 15, 2010, pp. 2319-2321, XP002721999, ISSN: 0936-5214, DOI: 10.1055/S-0030-1258025 [retreived on Aug. 3, 2010] cited in the application figure 2; compunds 1,2.

Remya Ramesh et al: "Enantiospiecific Synthesis of Both Enantiomers of the Longtailed Mailybug Pheromone and Their Evaluation in a New Zealand Vineyard", The Journal of Organic Chemistry, vol. 80, No. 15, Aug. 7, 2015, pp. 7785-7789, XP055306009, US ISSN: 0022-3263, DOI: 10.1021/acs.joc.5b01131 figures 2-3.

\* cited by examiner

ENANTIOSPECIFIC PROCESS FOR THE PREPARATION OF (R) AND (S) ENANTIOMERS OF SEX PHEROMONOES OF THE LONG TAILED MEALY BUG

CROSS-REFERENCE TO RELATED PATENT APPLICATIONS

The present application is a U.S. national stage application under 35 U.S.C. § 371 of PCT Application No. PCT/IN2016/050136, filed May 12, 2016, which claims priority to Indian Application No. 1323/DEL/2015, filed May 12, 2015, the entireties of which are incorporated herein by reference.

FIELD OF THE INVENTION

The present invention relates to an enantiospecific process for the preparation of enantiomers of sex pheromones. More particularly, the present invention relates to an enantiospecific process for the preparation of (R) and (S) enantiomers of sex pheromones of the long-tailed mealybug with high enantiopurity.

BACKGROUND AND PRIOR ART

Pheromones are chemicals released by an organism into its environment enabling it to communicate with other members of its own species. Mealybugs are known to spoil crops such as grapes, pears etc., especially the long-tailed mealybug. The long-tailed mealybug is scientifically known as *Pseudococcus longispinus* (Targioni-Tozzetti).

The racemic form of the pheromone was prepared synthetically by the Miller group after identifying the structure of isolated pheromone. Miller group has reported that 25 μg is sufficient to attract male mealybugs for three months and they can be trapped and killed; male population is thus decreased.

Pheromones play an important role in chemical communication among organisms. Various chiral and non-racemic pheromones have been identified since the late 1960s. Their enantioselective syntheses were achieved so as to establish the absolute configuration of the naturally occurring pheromones and also to clarify the relationship between absolute configuration and the bioactivity of the chiral pheromones. Synthesis of pheromones is an important and arising field of research to establish the structures and also to provide sufficient material to carry out biological studies. In general, natural pheromones are available in very limited quantities (usually in μg by killing several bugs) which restrict the extensive field trials. To overcome such constrain several methods have been reported in the literature to construct low molecular weight pheromones.

Article titled "Sex pheromonal activity of (+)-bornyl acetate and related compounds to the American cockroach" by Manabe S et al. published in *Journal of Chemical Ecology*, 1983; 9(3), pp 433-48 reports many compounds related to (+)-bornyl acetate (a sex pheromone mimic of the American cockroach) were synthesized and tested for sex pheromonal activity. All compounds except for esters of (+)- and (−)-borneol were inactive, whereas (+)-bornyl acetate (Ib) and propionate (Ic) showed the activity at 0.05 mg. Although (−)-bornyl propionate (IVc) is the enantiomer of Ic, it exhibited weak activity at 0.5 mg dose. On the basis of the behavioral assay results, important chemical factors in Ib for pheromonal activity were elucidated and are discussed in connection with another mimic, (+)-trans-verbenyl acetate. The M/F ratio index in EAG was evaluated for both active and inactive compounds. The index demonstrated a good correlation with the behavioral activity.

Article titled "Syntheses and determination of absolute configurations and biological activities of the enantiomers of the long-tailed mealybug pheromone" by Remya Ramesh et al. published in *Journal of Organic Chemistry*, 2013, 78, pp 6281-6284 reports preparation and assignment of absolute configurations to both enantiomers of the sex pheromone of the long-tailed mealybug, an irregular monoterpenoid with extraordinary biological activity. Comparison of the biological activities of both enantiomers and the racemate in field trials showed that the (S)-(+)-enantiomer was highly attractive to male mealybugs, strongly suggesting that female long-tailed mealybugs produce this enantiomer. The (R)-(−)-enantiomer was benign, being neither attractive nor inhibitory. Article titled "Synthesis of Verbenols and related alcohols and their pmr spectra with shift reagent" by Chikao Nisiuno et al. published in *Agricultural and Biological Chemistry*, 1979, 43 (9), pp 1967 1974 reports (+)-bornyl acetate (bicydicmonoterpenoid) and three other plant-derived compounds excite males of the American cockroach showing the typical sexual response mentioned.

Article titled "Useful Reactions in Modern Pheromone Synthesis" by Mori et al. published in *Current Organic Synthesis*, 2004, 1, pp 11-29 disclosed various aspects of pheromone synthesis where methodologies such as organoborane reactions, organotransition metal chemistry including olefin metathesis, asymmetric epoxidation, asymmetric dihydroxylation and other asymmetric chemical processes was demonstrated.

Article titled "The Baeyer-Villiger oxidation of aldehydes and ketones" by C. H. Hassall published in book titled "Organic Reactions" 2011, reports Baeyer and Vlliger showed that the oxidation of alicyclic ketones, menthone, tetrahydrocarvone, and camphor with permono-sulfuric acid led to the formation of lactones.

Article titled "Chemoselective reductive deoxygenation of α,β-unsaturated ketones and allyl alcohols" by Adusumilli Srikrishna et al. published in *Tetrahedron Letters*, 1995, 36 (13), pp 2347-2350 reports a simple and convenient procedure for a highly chemoselective reductive deoxygenation of α,β-unsaturated ketones and allyl alcohols to olefins by sodium cyanoborohydride and boron trifluorideetherate in dry THF.

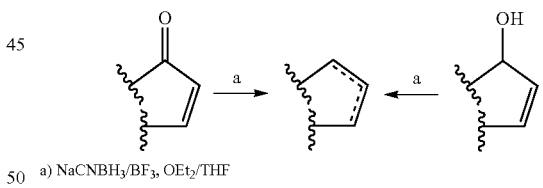

a) $NaCNBH_3/BF_3$, $OEt_2$/THF

Article titled "Pyridiniumchlorochromate. An efficient reagent for oxidation of primary and secondary alcohols to carbonyl compounds" by E. J. Corey et al. published in *Tetrahedron Letter*, 1975, 16, pp 2647-2650 reports pyridiniumchlorochromate is a readily available, stable reagent, that oxidizes a wide variety of alcohols to carbonyl compounds with high efficiency.

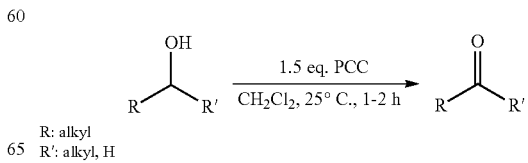

R: alkyl
R': alkyl, H

Article titled "Mechanisms of lactone hydrolysis in acidic conditions" by Rafael Gómez-Bombarelli et al. published in *Journal of Organic Chemistry*, 2013, 78 (14), pp 6880-6889 reports the acid-catalyzed hydrolysis of linear esters and lactones was studied using a hybrid supermolecule-polarizable continuum model (PCM) approach including up to six water molecules. The compounds studied included two linear esters, four β-lactones, two γ-lactones, and one δ-lactone: ethyl acetate, methyl formate, β-propiolactone, β-butyrolactone, β-isovalerolactone, diketene (4-methyleneoxetan-2-one), γ-butyrolactone, 2(5H)-furanone, and δ-valerolactone.

Article titled "Lanthanoids in organic synthesis. 6. Reduction of alpha-enones by sodium borohydride in the presence of lanthanoid chlorides: synthetic and mechanistic aspects." by Andre L. Gemal et al. published in *Journal of American Chemical Society*, 1981, 103 (18), pp 5454-5459 reports reduction of alpha-enones by sodium borohydride in the presence of lanthanoid chlorides.

Article titled "Reduction of ketones to hydrocarbons with triethylsilane: m-nitroethylbenzene" by James L. Fry et al. published in *Organic Synthesis*, 1981, 60, 108 et al. reports other carbonyl reduction methods include the familiar Clemmensen and Wolff-Kishner reactions. These are usually conducted for extended periods of time at elevated temperatures under strongly acidic or basic conditions, respectively. Mixed metal hydride-Lewis acid reagents constitute strong reducing systems that are often effective in the deoxygenation of diaryl ketones and some aryl alkyl ketones. However, even the mixed lithium aluminum hydride-aluminum chloride and sodium borohydride-boron trifluoride reagents reduce dialkyl ketones only to the corresponding alcohols, often with the formation of significant amounts of olefinic by-products.

Article titled "Acetic Anhydride" reports if the reaction is run at temperatures lower than 20° C., primary alcohols can be acetylated over secondary alcohols selectively. Under these conditions, tertiary alcohols are not acylated. Most alcohols, including tertiary alcohols, can be acylated by the addition of DMAP (4-Dimethylaminopyridine) and Acetyl Chloride to the reaction containing acetic anhydride and pyridine. In general, the addition of DMAP increases the rate of acylation by $10^4$ (eq 2).

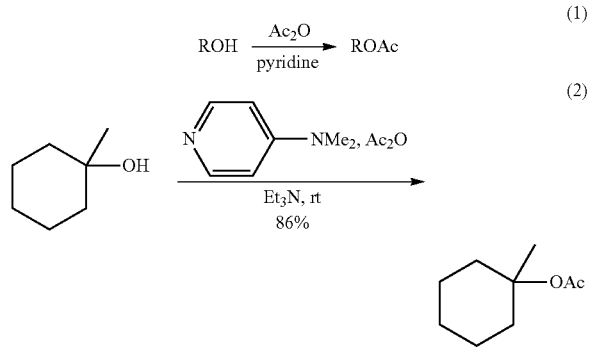

Article titled "Reduction Reactions" reports regioselective reduction of α,β-unsaturated carbonyl groups by luche reduction.

Article titled "Improved Synthesis of the Pheromone of the Long tailed Mealybug" by Jocelyn G. Millar et al. published in *Synlett* 2010, No. 15, pp 2319-2321 reports synthesis of pheromones involving Ireland-Claisen conditions in seven steps also discloses commercial development for detection, monitoring, and control of long-tailed mealybugs and the leafroll viruses that they vector.

Scheme 1

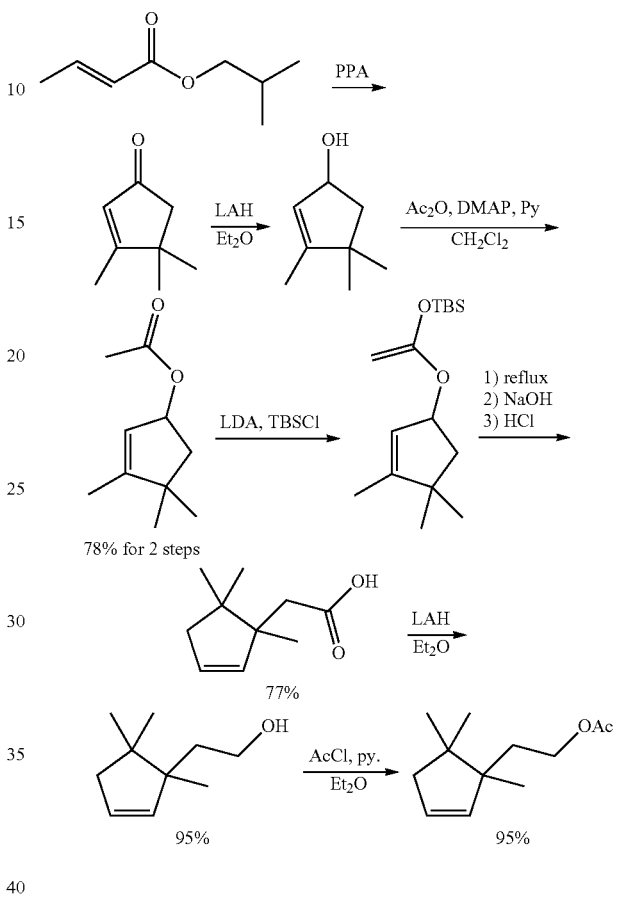

In view of prior art, pheromones are usually obtained in μg to mg quantities which are insufficient for the determination of their absolute configuration as well as for the biological studies to examine their practicality in the field. Also in view of the technical constraints to scale up the material and cumbersome resolution, the present inventors have developed efficient synthesis for preparation of enantiomers of sex pheromones in good yields.

OBJECTIVE OF THE INVENTION

The main objective of the present invention is to provide an enantiospecific process for the preparation of enantiomers of sex pheromones of the long-tailed mealybug with high enantiopurity.

Another objective of the present invention is to provide novel intermediates which are useful for preparation of enantiomers of sex pheromones of the long-tailed mealybug.

SUMMARY OF THE INVENTION

Accordingly, the present invention provides an enantiospecific process for the preparation of (R) and (S) enantiomers of sex pheromones of the long-tailed mealybug with high enantiopurity.

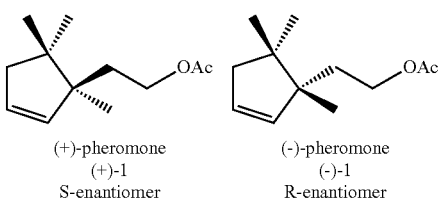

(+)-pheromone (+)-1 S-enantiomer (−)-pheromone (−)-1 R-enantiomer

In an embodiment, the present invention further provides novel intermediates which are useful for preparation of enantiomers of sex pheromones of the long-tailed mealybug.

DETAILED DESCRIPTION OF THE INVENTION

The invention will now be described in detail in connection with certain preferred and optional embodiments, so that various aspects thereof may be more fully understood and appreciated.

The expression '(−)-1' or '(R)-1' or '(−) pheromone' or '(R)-enantiomer' or '(R)-pheromone' or '(−) 2-(1,5,5-trimethylcyclopent-2-en-1-yl)ethyl acetate' or '2-[(1R)-1,5,5-trimethylcyclopent-2-en-1-yl]ethyl acetate' are used interchangeably throughout the specification.

Similarly, the expression '(+)-1' or '(S)-1' or '(+) pheromone' or '(S)-enantiomer' or '(S)-pheromone' or '(+) 2-(1,5,5-trimethylcyclopent-2-en-1-yl)ethyl acetate' or "2-[(1S)-1,5,5-trimethylcyclopent-2-en-1-yl]ethyl acetate" are used interchangeably throughout the specification and the same may be appreciated as such by the person skilled in the art.

The present invention provides a novel synthetic route for the preparation of enantiomers (represented by (+) 1 and (−) 1 of sex pheromones of the long-tailed mealybug with high enantiopurity having significant biological activity.

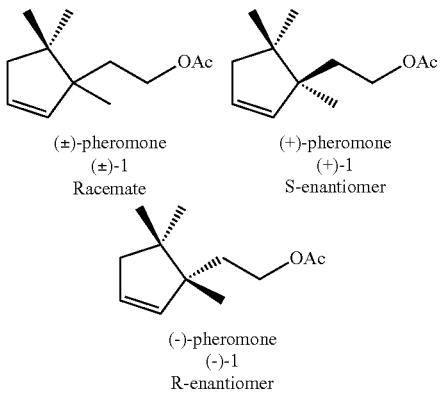

(±)-pheromone (±)-1 Racemate (+)-pheromone (+)-1 S-enantiomer (−)-pheromone (−)-1 R-enantiomer In an embodiment, the present invention provides an enantiospecific process for preparation of (R) and (S) enantiomers of sex pheromones of the long-tailed mealybug comprising the steps of:
a) oxidizing (+)bornylacetate(+)-(2) using suitable oxidizing agent in presence of sulfuric acid ($H_2SO_4$) followed by acetate hydrolysis using suitable base to obtain compound (+)-3;
b) oxidizing alcohol (+)-3 of step (a) using Cornforth reagent to obtain lactone (+)-4;
c) hydrolyzing lactone(+)-4 of step (b) with suitable hydrolyzing agent in methanol to give α-β-unsaturated cyclopentenone(+)-5;
d) subjecting the cyclopentenone(+)-5 of step (c) to luche reduction to afford allylic alcohol 6';
e) subjecting the allylic alcohol 6' of step (d) to deoxygenation using dehydroxylation agent in tetrahydrofuran (THF) followed by reduction to afford 7b' and (+)-7a;
f) subjecting alcohol (+)-7a of step (e) to acylation to afford compound (+)-pheromone.

Using similar procedure, (−)-pheromone can be synthesized starting from (−)bornylacetate (−)-(2) through the intermediacy of (−)-3, (−)-4, (−)-5, 6 and (−)7a.

In preferred embodiment, said suitable oxidizing agent in step (a) is selected from hydrogen peroxide, preferably the oxidizing agent is hydrogen peroxide in acetic acid.

In another preferred embodiment, said suitable base in step (a) is an inorganic base; said base is selected from sodium carbonate, sodium bicarbonate and calcium carbonate, preferably said base is potassium carbonate.

The Cornforth reagent of step (b) is Pyridiniumdichromate (PDC).

In still another preferred embodiment, said suitable hydrolyzing agent of step (c) is p-Toluenesulfonic acid.

The luchereduction in step (d) is carried out in presence of cerium (III) chloride heptahydrate and sodium borohydride.

In yet another preferred embodiment, said deoxygenation agent of step (e) issodium cyanoborohydride and boron trifluoride-etherate.

The acylation reaction in step (f) is carried out using acylating agent, base and catalyst.

In still yet another preferred embodiment, said acylating agent of step (f) is selected from acetic anhydride, acetyl chloride, preferably said acylating agent is acetic anhydride.

In still yet another preferred embodiment, said base is selected from the group consisting of dimethylamine, diethylamine, trimethylamine, triethylamine, tributylamine, dimethylaniline, pyridine or mixtures thereof, preferably triethylamine in presence of suitable acylation catalyst such as 4-dimethylaminopyridine or the like.

In still yet another preferred embodiment, the present invention provides an enantiospecific process for preparation of (R)-(−)-pheromone of the long-tailed mealybug with high enantiopurity comprising the steps of:
a) adding acetic acid, hydrogen peroxide and $H_2SO_4$ to (−)5-oxobornylacetate and stirred for the time ranging from 24 to 26 h at the temperature ranging from 25 to 30° C. followed by work up, concentration and addition of potassium carbonate and further stirring for the time period ranging from 3 to 4 h to obtain (3aS,5S,6aR)-5-hydroxy-3a,4,4-trimethylhexahydro-2H-cyclopenta[b]furan-2-one ((−)-3);
b) adding pyridinium dichromate to a solution of compound of step (a) followed by stirring for the time period ranging from 8 to 10 h at the temperature ranging from 25 to 30° C. to obtain 3aS,6aR)-3a,4,4-trimethyltetrahydro-2H-cyclopenta[b]furan-2,5(3H)-dione ((−)-4);
c) refluxing, the reaction mixture of P-Toluene sulphonic acid and a solution of compound of step (b) in methanol for the time period ranging from 24 to 26 h at the temperature ranging from 65° C. to 70° C. to obtain methyl (R)-2-(1,5,5-trimethyl-4-oxocyclopent-2-en-1-yl)acetate ((−)-5);
d) adding cerium(III) chloride heptahydrate and sodium borohydride to a cooled solution of compound of step (c) in methanol followed by stirring the reaction mixture for the time period ranging from 1 to 2 h at the temperature ranging from 25° C. to 30° C. to obtain methyl 2-((1R)-4-hydroxy-1,5,5-trimethylcyclopent-2-en-1-yl)acetate (6);

e) adding boron trifluoride diethyl etherate and sodiumcyanoborohydride to a cooled solution of compound of step (d) in tetrahydrofuran followed by refluxing the reaction mixture for the time period ranging from 8 to 10 h at the temperature ranging from 66° C. to 70° C. to obtain methyl (R)-2-(1,5,5-trimethylcyclopent-2-en-1-yl)acetate;

f) adding lithium aluminium hydride (LAH) to a cold solution of compound of step (e) in tetrahydrofuran followed by stirring the reaction mixture for the time period ranging from 2 to 3 h at the temperature ranging from 25° C. to 30° C. to obtain (R)-2-(1,5,5-trimethylcyclopent-2-en-1-yl)ethan-1-ol ((−)-(7a);

g) stirring the reaction mixture of compound of step (f) in dichloromethane, triethylamine, acetic anhydride and 4-dimethylaminopyridine for the time period ranging from 3 to 4 h at the temperature ranging from 25° C. to 30° C. to obtain (R)-2-(1,5,5-trimethylcyclopent-2-en-1-yl)ethyl acetate.

The enantiospecific process for the preparation of (R)-(−)-pheromone of the long-tailed mealybug is as shown in scheme 3 below:

Scheme 3: Synthesis of (R)-(−)-pheromone

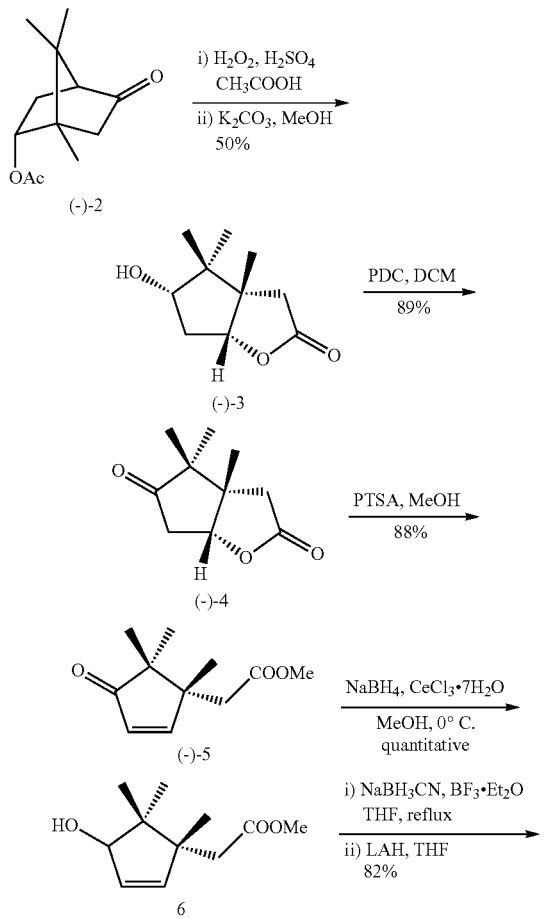

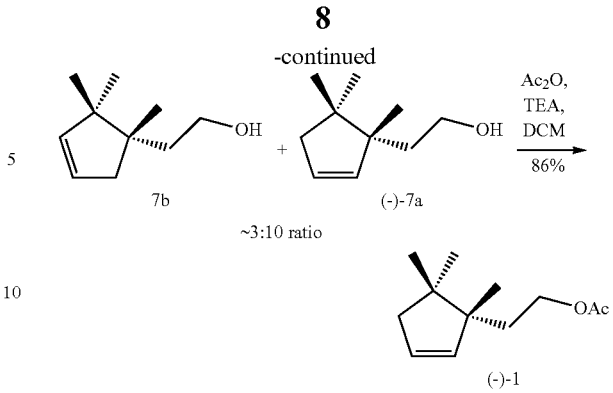

The ketone (−)-(2) is subjected to Baeyer-Villiger oxidation using $H_2O_2$ in acetic acid in presence of $H_2SO_4$ followed by acetate hydrolysis using $K_2CO_3$. Under these conditions, we obtained the compound (−)-3 which is confirmed by X-ray crystal structure analysis. The alcohol (−)-3 is oxidized to ketone (−)-4 using Pyridiniumdichromate (PDC). The lactone (−)-4 is hydrolysed with p-Toluenesulfonic acid (PTSA) in methanol to give α-β-unsaturated cyclopentenone (−)-5. The allylic alcohol 6 obtained by luche reduction of (−)-5 is subjected to dehydroxylation using $BF_3$.etherate and sodiumcyanoborohydride in dry THF to give a mixture of regioisomeric products. The ester is reduced with LAH and the regioisomers7b and (−)-7a can be separated at this stage. The alcohol (−)-7a is acylated to give the target compound (−)-pheromone. The same route is followed for the synthesis of the other antipode (S)-(+)-pheromone. The optical rotations also showed the same magnitude but with an inverse sign.

The regioisomeric mixture obtained in the step (e) is used to prepare the title compound. The compound is then dissolved in tetrahydrofuran (THF), cooled to 0° C. followed by addition of Lithium aluminium hydride (LAH) and stirred at room temperature for 2 h. The reaction mixture was quenched with saturated Sodium sulfate ($Na_2SO_4$), ethyl acetate was added and the organic layer was separated, dried and purified by column chromatography. Both the regioisomers are separated by flash column chromatography.

In still yet another preferred embodiment, the present invention provides an enantioselective process for preparation of (S)-(+)-pheromone of the long-tailed mealybug with high enantiopurity wherein the process comprising the steps of:

a) adding acetic acid, hydrogen peroxide and $H_2SO_4$ to (+)-5-oxobornylacetate (+)-2 and stirred for the time period ranging from 24 to 26 h at the temperature ranging from 25° C. to 30° C. followed by work up, removal of solvent and addition of potassium carbonate and further stirring for the time period ranging from 3 to 4 h to obtain (3aS,5S,6aR)-5-hydroxy-3a,4,4-trimethylhexahydro-2H-cyclopenta[b]furan-2-one ((+)-3);

b) adding pyridinium dichromate to a solution of compound of step (a) followed by stirring for the time period ranging from 8 to 10 h at the temperature ranging from 25° C. to 30° C. to obtain (3aS,6aR)-3a,4,4-trimethyltetrahydro-2H-cyclopenta[b]furan-2,5(3H)-dione ((+)-4);

c) refluxing the reaction mixture of p-toluene sulphonic acid and a solution of compound of step (b) in methanol for the time period ranging from 24 to 26 h at the temperature ranging from 65° C. to 70° C. to obtain methyl (S)-2-(1,5,5-trimethyl-4-oxocyclopent-2-en-1-yl)acetate ((+)-5);

d) adding Cerium(III) chloride heptahydrate and sodium borohydride to a cold solution of compound of step (c) in methanol followed by stirring the reaction mixture for the time period ranging from 1 to 2 h at the temperature ranging from 25° C. to 30° C. to obtain methyl 2-((1S)-4-hydroxy-1,5,5-trimethylcyclopent-2-en-1-yl)acetate (6');

e) adding boron trifluoride, diethyl etherate and sodium-cyanoborohydride to a cold solution of compound of step (d) in tetrahydrofuran followed by refluxing the reaction mixture for 8 to 10 hours at the temperature ranging from 66° C. to 70° C. to obtain methyl (S)-2-(1,5,5-trimethylcyclopent-2-en-1-yl)acetate;

f) adding lithiumaluminiumhydride (LAH) to a cold solution of compound of step (e) in tetrahydrofuran followed by stirring the reaction mixture for the time period ranging from 2 to 3 h at the temperature ranging from 25° C. to 30° C. to obtain (S)-2-(1,5,5-trimethyl-cyclopent-2-en-1-yl)ethan-1-ol ((+)-(7a);

g) stirring the reaction mixture of compound of step (f) in dichloromethane, triethylamine, acetic anhydride and 4-Dimethylaminopyridine for the time period ranging from 3 to 4 that the temperature ranging from 25° C. to 30° C. to obtain (S)-2-(1,5,5-trimethylcyclopent-2-en-1-yl) ethyl acetate.

The enantiospecific process for preparation of (S)-(+)-pheromone of the long-tailed mealybug is as shown in scheme 4 below:

Scheme 4: Synthesis of (S)-(+)-pheromone

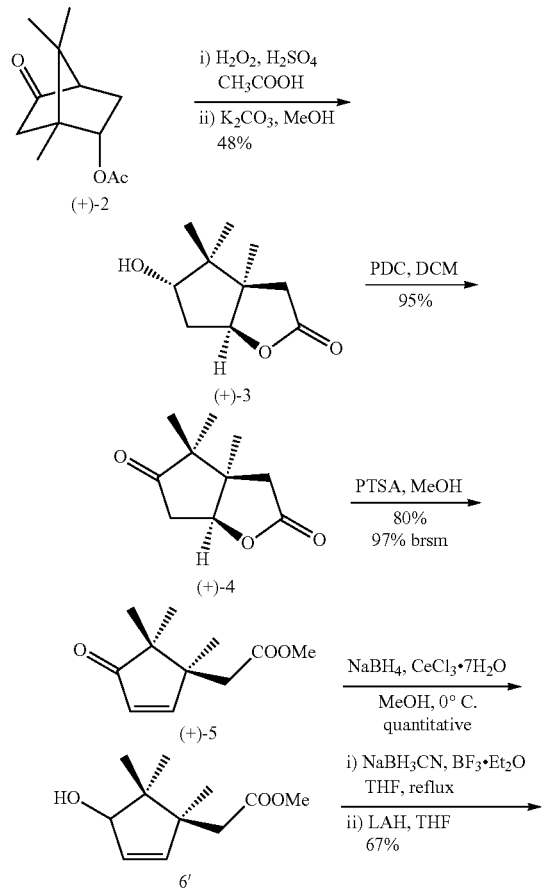

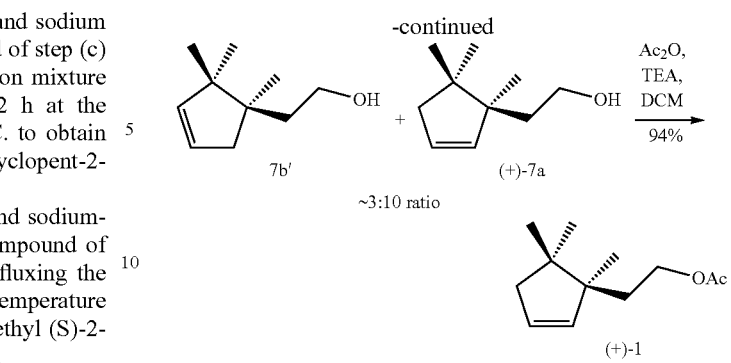

In another embodiment, the present invention provides novel intermediates which are useful for preparation of enantiomers of sex pheromones of the long-tailed mealybug.

In preferred embodiments, said novel intermediates are selected from (3aS,5S,6aR)-5-hydroxy-3a,4,4-trimethyl-hexahydro-2H-cyclopenta[b]furan-2-one, (3aS,6aR)-3a,4,4-trimethyltetrahydro-2H-cyclopenta[b]furan-2,5(3H)-dione, methyl-2-(1,5,5-trimethyl-4-oxocyclopent-2-en-1-yl)acetate, methyl 2-((1R)-4-hydroxy-1,5,5-trimethylcyclopent-2-en-1-yl)acetate, methyl 2-(1,5,5-trimethylcyclopent-2-en-1-yl)acetate, 2-(1,5,5-trimethylcyclopent-2-en-1-yl)ethan-1-ol.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of (3aS,5S,6aR)-5-hydroxy-3a,4,4-trimethylhexahydro-2H-cyclopenta[b]furan-2-one ((−)-3)

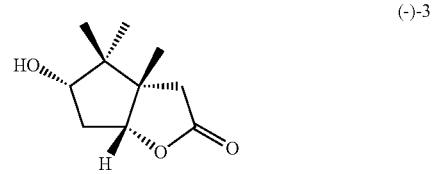

Acetic acid (6 mL), $H_2O_2$ (35 wt % in water, 5 mL) and $H_2SO_4$ (1 mL) was taken in an RB to which (−)-2 (1.9 g, 9.03 mmol) was added and stirred at room temperature for 24 h. Ethyl acetate was added and the aqueous layers was extracted thrice. The organic layer was dried and the solvent was evaporated under reduced pressure. The crude thus obtained was dissolved in methanol, added $K_2CO_3$ and stirred at room temperature for 3 h. The reaction mixture was passed through celite and the filtrate was concentrated and purified by column chromatography (230-400 silica gel) using 25-30% Ethylacetate-pet ether to afford the product as a colorless crystalline solid (832 mg, 50%). The structure was unambiguously confirmed by X-ray crystal structure analysis. Mp=224-226° C.; $[\alpha]_D^{29}$=−9.2 (c=0.33); $^1$H NMR (400 MHz, $CDCl_3$) δ ppm 4.54 (d, J=8.6 Hz, 1H), 3.90 (d, J=5.1 Hz, 1H), 3.34 (d, J=18.1 Hz, 1H), 2.54-2.46 (m, 1H), 2.06 (d, J=18.1 Hz, 1H), 1.86 (d, J=15.9 Hz, 1H), 1.13 (s, 3H), 1.03 (s, 3H), 0.84 (s, 3H); $^{13}$C NMR (100 MHz, $CDCl_3$)

δ ppm 177.8, 90.5, 81.4, 50.71, 46.5, 40.2, 39.8, 24.2, 22.2, 18.3; IR $v_{max}$ (thin film applied as CHCl$_3$ solution) 3470 (broad peak), 2969, 1764, 1069 cm$^{-1}$; HRMS (ESI): m/z calculated for C$_{10}$H$_{16}$O$_3$Na [M+Na]$^+$ 207.0992, found 207.0985.

A. X-Ray Crystal Structure Details of (−)-3:

Single crystals of compound (−)-3 was obtained from chloroform. X-ray intensity data were collected on a APEX II CCD diffractometer with graphite-monochromatized (Mo Kα=0.71073 Å) radiation at room temperature 296(2) K. The X-ray generator was operated at 50 kV and 30 mA. Diffraction data were collected with a ω scan width of 0.5° and at different settings of φ and 2θ. The sample-to-detector distance was fixed at 5.00 cm. The X-ray data acquisition was monitored by APEX II program suite.[14] All the data were corrected for Lorentz-polarization and absorption effects using SAINT and SADABS programs integrated in APEX II program package.[14] The structures were solved by direct method and refined by full matrix least squares, based on F$^2$, using SHELX-97.[15] ORTEP diagrams was generated using XSHELL program integrated in SHELXTL package[15] with 30% probability displacement ellipsoids and H atoms are shown as small spheres of arbitrary radii. All the H-atoms were placed in geometrically idealized position (C—H=0.97 Å for the methylene H-atom, C—H=0.96 Å for the methyl H-atom, C—H=0.98 Å for the methine H-atom and O—H=0.82 Å for the hydroxyl H-atom) and constrained to ride on their parent atoms [U$_{iso}$(H)=1.2 U$_{eq}$(C) for the methylene and methine group, U$_{iso}$(H)=1.5 U$_{eq}$(C) for the methyl group and U$_{iso}$(H)=1.5 U$_{eq}$(O) for the hydroxyl group].

B. Crystallographic Data for (−)-3:

(C$_{10}$H$_{16}$O$_3$): M=184.23, Crystal dimensions 0.64×0.60×0.20 mm$^3$, orthorhombic, space group P2$_1$2$_1$2$_1$, a=6.9872 (7), b=11.6575(12), c=11.8586(12) Å, V=965.92(17) Å$^3$, Z=4, ρ$_{calcd}$=1.267 gcm$^{-3}$, μ (Mo—K$_α$)=0.092 mm$^{-1}$, F(000)=400, 2θ$_{max}$=50.000, T=296(2) K, 5178 reflections collected, 1648 unique, 1532 observed (I>2σ (I)) reflections, 122 refined parameters, R value 0.0329, wR2=0.0806, (all data R=0.0356, wR2=0.0824), S=1.091, minimum and maximum transmission 0.943 and 0.982; maximum and minimum residual electron densities +0.09 and −0.11 e Å$^{-3}$.

Example 2: Synthesis of (3aS,6aR)-3a,4,4-trimethyltetrahydro-2H-cyclopenta[b]furan-2,5(3H)-dione ((−)-4)

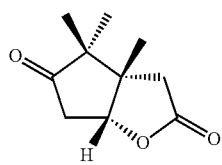

(−)-4

To a solution of (−)-3 (1.2 g, 6.5 mmol) in dry DCM, molecular sieves was added followed by PDC (3.7 g, 9.8 mmol) and stirred at room temperature for overnight. The reaction mass was filtered through celite. The filtrate was washed with 1N HCl, dried and concentrated. The crude mass was purified by column chromatography (100-200 silica gel) using 15% ethyl acetate-pet ether to give the compound as a white crystalline solid (1.05 g, 89% yield). Mp=169-171° C.; [α]$_D$$^{29}$=−98.28 (c=0.32); $^1$H NMR (400 MHz, CDCl$_3$) δ ppm 4.79 (dd, J=9.0, 4.2 Hz, 1H), 3.02 (dd, J=20.3, 8.8 Hz, 1H), 2.44 (dd, J=20.3, 4.2 Hz, 1H), 2.32 (AB quartet, 2H), 1.27 (s, 3H), 1.08 (s, 3H), 1.02 (s, 3H); $^{13}$C NMR (100 MHz, CDCl$_3$) δ ppm 216.3, 175.3, 82.7, 52.4, 50.1, 41.1, 39.0, 21.2, 19.3, 18.8; IR $v_{max}$ (thin film applied as CHCl$_3$ solution) 2973, 2884, 1783, 1747, 1460, 1288, 1177, 1050 cm$^{-1}$; HRMS (ESI): m/z calculated for C$_{10}$H$_{15}$O$_3$[M+H]$^+$ 183.1016, found 183.1011.

Example 3: Synthesis of methyl (R)-2-(1,5,5-trimethyl-4-oxocydopent-2-en-1-yl)acetate ((−)-5)

(−)-5

The compound (−)-4 was dissolved in dry methanol, PTSA was added and refluxed at 65° C. for 24 h. The reaction mass was cooled and solvent was removed under reduced pressure. Water and DCM was added and the organic layer was separated, aqueous layer was extracted with DCM and the combined organics were dried and concentrated under reduced pressure. The pure product was obtained by column chromatography (silica gel 100-200) using 10% ethyl acetate-petether to afford the product as a colourless liquid (475 mg, 88% yield) along with recovery of starting material (30 mg). [α]$_D$$^{29}$=−4.45 (c=0.34); $^1$H NMR (500 MHz, CDCl$_3$) δ ppm 7.71 (d, J=5.8 Hz, 1H), 6.08 (d, J=5.8 Hz, 1H), 3.71 (s, 3H), 2.51 (d, J=14.9 Hz, 1H), 2.39 (d, J=14.9 Hz, 1H), 1.18 (s, 3H), 1.09 (s, 3H), 1.06 (s, 3H); $^{13}$C NMR (125 MHz, CDCl$_3$) δ ppm 213.5, 171.9, 168.5, 129.0, 51.6, 51.3, 48.5, 41.5, 23.0, 22.7, 20.9; IR $v_{max}$ (thin film applied as CHCl$_3$ solution) 2969, 2883, 1715, 1594, 1203 cm$^{-1}$; HRMS (ESI): m/z calculated for C$_{11}$H$_{17}$O$_3$ [M+H]$^+$ 197.1172, found 197.1173.

Example 4: Synthesis of methyl 2-((1R)-4-hydroxy-1,5,5-trimethylcyclopent-2-en-1-yl)acetate (6)

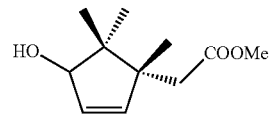

6

A solution of (−)-5 (200 mg, 1.02 mmol) in dry methanol was cooled to 0° C., added CeCl$_3$.7H$_2$O (418 mg, 1.12 mmol), followed by sodiumborohydride (77 mg, 2.04 mmol) and stirred at room temperature for 1 h. The reaction mass was cooled to 0° C., quenched with sat. NH$_4$Cl and methanol was removed in rotary evaporator. Ethyl acetate was added and the aqueous layer was extracted, dried over Na$_2$SO$_4$ and concentrated to give the product as a colourless liquid (200 mg, quantitative). Data for major diastereomer: $^1$H NMR (400 MHz, CDCl$_3$) δ ppm 5.98 (d, J=5.6 Hz, 1H), 5.78-5.74 (m, 1H), 4.27 (d, J=13.2 Hz, 1H), 3.66 (s, 3H), 2.40 (AB quartet, 2H), 1.00 (s, 3H), 0.96 (s, 3H), 0.93 (s, 3H); $^{13}$C NMR (100 MHz, CDCl$_3$) δ ppm 173.2, 141.8, 130.6, 84.4, 51.3, 49.6, 47.3, 43.4, 23.6, 20.2, 17.8.

Example 5: Synthesis of methyl (R)-2-(1,5,5-trimethylcyclopent-2-en-1-yl)acetate

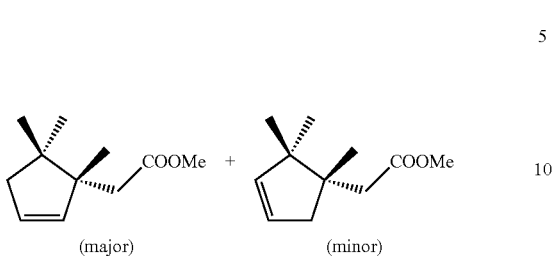

(major)    (minor)

A solution of 6 (70 mg, 0.353 mmol) in dry THF was cooled to 0° C., added BF$_3$.Et$_2$O (0.13 mL, 1.059 mmol) followed by sodiumcyanoborohydride (66 mg, 1.059 mmol) and refluxed at 66° C. for overnight. The reaction was quenched with 2N NaOH, added DCM and the organic layer was separated. It was then dried, concentrated and purified by column chromatography (silica gel 230-400 gel) using 2% ethyl acetate-petether to give the product as a mixture with its regioisomer (55 mg, 86% combined yield, 10:3 ratio by NMR). Data for major isomer: $^1$H NMR (400 MHz, CDCl$_3$) δ ppm 5.80-5.76 (m, 1H), 5.68-5.65 (m, 1H), 3.68 (s, 3H), 2.44-2.07 (m, 4H), 0.99 (s, 6H), 0.96 (s, 3H); $^{13}$C NMR (100 MHz, CDCl$_3$) δ ppm 173.6, 138.7, 127.9, 51.2, 49.8, 46.7, 44.1, 40.6, 24.4, 24.0, 19.8.

Example 6: Synthesis of (R)-2-(1,5,5-trimethylcyclopent-2-en-1-yl)ethan-1-ol ((−)-(7a)

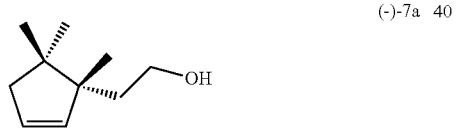

(−)-7a

The regioisomeric mixture obtained in the above step was used to prepare the title compound. The compound (50 mg, 0.275 mmol) was dissolved in dry THF, cooled to 0° C., added LAH (31 mg, 0.824 mmol) and stirred at room temperature for 2 h. The reaction mixture was quenched with saturated Na$_2$SO$_4$, ethyl acetate was added and the organic layer was separated, dried and purified by column chromatography (silica gel 230-400 mesh) using 5% ethyl acetate-petether to give the product as a colourless liquid (40 mg, 95% along with its regioisomer). Both the regioisomers could be separated by flash column chromatography although they were inseparable in TLC. [α]$_D^{26}$=−10.36 (c=1.14); $^1$H NMR (400 MHz, CDCl$_3$) δ ppm 5.65-5.63 (m, 1H), 5.59-5.57 (m, 1H), 3.81-3.68 (m, 2H), 2.15-2.13 (m, 2H), 1.73-1.65 (m, 1H), 1.59-1.52 (m, 1H), 0.97 (s, 3H), 0.95 (s, 3H), 0.90 (s, 3H); $^{13}$C NMR (100 MHz, CDCl$_3$) δ ppm 139.1, 128.0, 60.8, 49.5, 46.8, 44.0, 39.2, 24.8, 23.9, 19.4; HRMS (ESI): m/z calculated for C$_{10}$H$_{19}$O [M+H]$^+$ 155.1435, found 155.1430.

Example 7: Synthesis of (S)-2-(1,2,2-Trimethylcydopent-3-en-1-yl)ethan-1-ol((+)-7b)

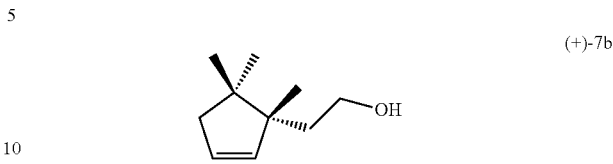

(+)-7b

[α]$_D^{25}$+14.5 (c 0.17, CHCl$_3$); $^1$H NMR (500 MHz, CDCl$_3$) δ ppm 5.54-5.51 (m, 1H), 5.44-5.43 (m, 1H), 3.79-3.64 (m, 2H), 2.32-2.28 (m, 1H), 2.03-2.00 (m, 1H), 1.73-1.60 (m, 2H), 0.92 (s, 3H), 0.90 (s, 3H), 0.90 (s, 3H).

Example 7: Synthesis of (R)-2-(1,5,5-trimethylcydopent-2-en-1-yl) ethyl acetate

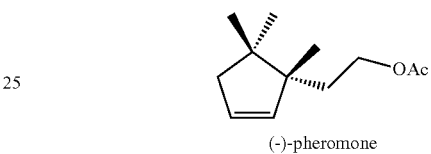

(−)-pheromone

To a solution of (−)-7a (10 mg, 0.065 mmol) in dry DCM, triethylamine (36 μL, 0.26 mmol) and acetic anhydride (12 μL, 0.13 mmol) was added followed by a pinch of DMAP and stirred at room temperature for 3 h. Water was added and the organic layer was separated, dried, concentrated and purified by column chromatography (100-200 silica gel) using 20% DCM-pentane to afford the product as a colourless liquid (11 mg, 86%). [o]D$^{25}$-20.6 (c 0.33, CHCl$_3$); $^1$H NMR (400 MHz, CDCl$_3$) δ ppm 5.66-5.63 (m, 1H), 5.58-5.56 (m, 1H), 4.24-4.07 (m, 2H), 2.14 (t, J=2.2 Hz, 2H), 2.06 (s, 3H), 1.75-1.68 (m, 1H), 1.63-1.54 (m, 1H, merged with moisture peak), 0.97 (s, 3H), 0.96 (s, 3H), 0.91 (s, 3H); $^{13}$C NMR (100 MHz, CDCl$_3$) δ ppm 171.2, 138.7, 128.2, 62.8, 49.4, 46.8, 44.0, 34.5, 24.6, 24.0, 21.1, 19.4; HRMS (ESI): m/z calculated for C$_{12}$H$_{20}$O$_2$Na [M+Na]$^+$ 219.1356, found 219.1355.

Example 8: Synthesis of (S)-(+)-pheromone

The same route was followed for the synthesis of the other antipode (S)-(+)-pheromone starting from (+)-2. The NMR data of all the compounds were found to be exactly matching. The optical rotations also showed the same magnitude but with an inverse sign. The data of known compounds were compared with literature reports and found to be identical.

Example 9: Synthesis of (3aR,5R,6aS)-5-Hydroxy-3a,4,4-trimethylhexahydro-2H-cyclopenta[b]furan-2-one (+)-3

Yield: 48%; [α]$_D^{28}$+6.8 (c 0.34, CHCl$_3$)

Example 10: Synthesis of (3aR,6aS)-3a,4,4-Trimethyltetrahydro-2H-cyclopenta[b]furan-2,5(3H)-dione (+)-4

Yield: 95%; [α]$_D^{28}$+98.3 (c 0.27, CHCl$_3$)

Example 11: Synthesis of Methyl(S)-2-(1,5,5-trimethyl-4-oxocydopent-2-en-1-yl)acetate (+)-5

Yield: 80%, 97% brsm; $[\alpha]_D^{25}$ +4.5 (c 0.50, CHCl$_3$)

Example 12: Synthesis of (S)-2-(1,5,5-Trimethylcyclopent-2-en-1-yl)ethan-1-ol ((+)-7a)

$[\alpha]_D^{26}$ +11.3 (c 0.30, CHCl$_3$)

Example 13: Synthesis of (R)-2-(1,2,2-Trimethylcydopent-3-en-1-yl)ethan-1-ol((−)-7b')

$[\alpha]_D^{24}$ -13.8 (c 0.17, CHCl$_3$); $^1$H NMR (400 MHz, CDCl$_3$) δ ppm 5.54-5.51 (m, 1H), 5.44-5.43 (m, 1H), 3.79-3.64 (m, 2H), 2.32-2.28 (m, 1H), 2.03-1.98 (m, 1H), 1.73-1.60 (m, 2H), 0.91 (s, 3H), 0.90 (s, 3H), 0.89 (s, 3H); $^{13}$C NMR (100 MHz, CDCl$_3$) δ ppm 141.6, 126.2, 61.1, 48.7, 44.9, 44.7, 39.6, 23.8, 22.3, 22.2.

Example 14: Synthesis of (S)-2-(1,5,5-Trimethylcydopent-2-en-1-yl)ethyl acetate Yield: 94%; $[o]_D^{32}$ +23.7 (c 0.33, CHCl$_3$)

ADVANTAGES OF INVENTION

Useful in the field of agriculture to improve the quantitative and qualitative production.
Useful in crop protection and may help in protecting high value crops such as grapes, citrus, apples, pears, pomegranate, cotton and ornamental plants.

We claim:

1. An enantiospecific process for preparation of (R) and (S) enantiomers of sex pheromones of the long tailed mealybug, said process consisting of steps:
   a) oxidizing (+) oxobornylacetate(+)-(2) or (−)-(2) using H$_2$O$_2$/H$_2$SO$_4$ in acetic acid followed by acetate hydrolysis using a base to obtain compound (+)-3 or (−)-3 respectively;

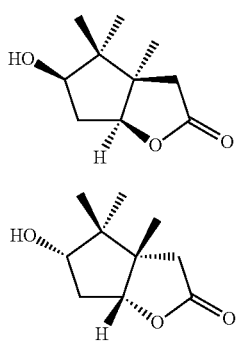

(+)-3

(−)-3 b) oxidizing alcohol (+)-3 or (−)-3 of step (a) using cornforth reagent to obtain lactone (+)-4 or (−)-4 respectively;

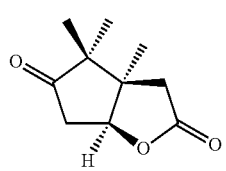

(+)-4

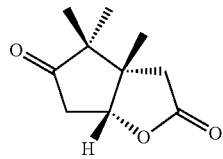

(−)-4 c) hydrolyzing lactone(+)-4 or (−)-4 of step (b) by refluxing in methanol in presence of p-toluenesulphonic acid (PTSA) to give α,β-unsaturated cyclopentenone(+)-5 or (−)-5 respectively;

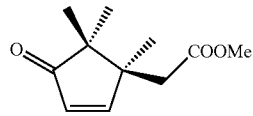

(+)-5

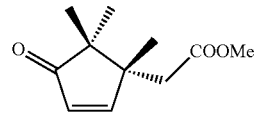

(−)-5 d) subjecting the cyclopentenone(+)-5 or (−)-5 of step (c) to Luche reduction to afford allylic alcohol 6' or 6;

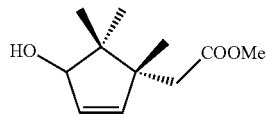

6

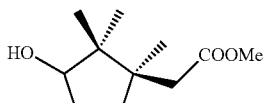

6' e) subjecting the allylic alcohol 6' or 6 of step (d) to deoxygenation using boron trifluoride-etherate and sodium cyanoborohydride in tetrahydrofuran (THF) followed by reduction using lithium aluminum hydride to afford 7b' and (+)-7a or 7b and (−)-7a respectively;

7b'

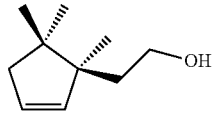

(+)-7a

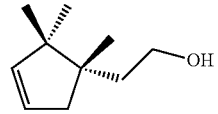

7b

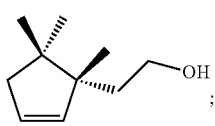

and f) subjecting alcohol (+)-7a or (−)7a of step (e) to acylation to afford compound (+)- or (−)-pheromone respectively

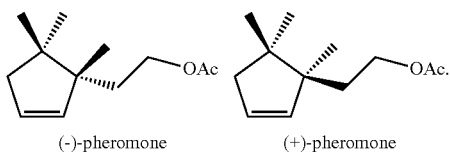

2. The process as claimed in claim 1, wherein said base in step (a) is an inorganic base; said base is selected from sodium carbonate, sodium bicarbonate, calcium carbonate, and potassium carbonate.

3. The process as claimed in claim 1, wherein said acylation reaction in step (f) is carried out for acetylation of an alcohol using acylating agent, base and catalyst; wherein said acylating agent is selected from acetic anhydride, acetyl chloride; wherein said base in step (f) is selected from the group consisting of dimethylamine, diethylamine, trimethylamine, triethylamine, tributylamine, dimethylaniline, pyridine or mixtures thereof; and said catalyst used in step (f) is 4-dimethylaminopyridine.

4. The process as claimed in claim 1, wherein said process for preparation of (R)-(−)-pheromone consists the steps of:
a) adding acetic acid, hydrogen peroxide and $H_2SO_4$ to (−)5-oxobornylacetate and stirred for the time ranging from 24 to 26 h at the temperature ranging from 25 to 30° C. followed by work up, concentration and addition of potassium carbonate and further stirring for the time period ranging from 3 to 4 h to obtain (3aS,5S,6aR)-5-hydroxy-3a,4,4-trimethylhexahydro-2H-cyclopenta[b]furan-2-one ((−)-3);
b) adding pyridinium dichromate to a solution of compound of step (a) followed by stirring for the time period ranging from 8 to 10 h at the temperature ranging from 25 to 30° C. to obtain 3aS,6aR)-3a,4,4-trimethyltetrahydro-2H-cyclopenta[b]furan-2,5(3H)-dione ((−)-4);
c) refluxing, the reaction mixture of p-toluene sulphonic acid and a solution of compound of step (b) in methanol for the time period ranging from 24 to 26 h at the temperature ranging from 65° C. to 70° C. to obtain methyl (R)-2-(1,5,5-trimethyl-4-oxocyclopent-2-en-1-yl)acetate ((−)-5);
d) adding cerium(III) chloride heptahydrate and sodium borohydride to a cooled solution of compound of step (c) in methanol followed by stirring the reaction mixture for the time period ranging from 1 to 2 h at the temperature ranging from 25° C. to 30° C. to obtain methyl 2-((1R)-4-hydroxy-1,5,5-trimethylcyclopent-2-en-1-yl)acetate (6);
e) adding boron trifluoride diethyl etherate and sodiumcyanoborohydride to a cooled solution of compound of step (d) in tetrahydrofuran followed by refluxing the reaction mixture for the time period ranging from 8 to 10 h at the temperature ranging from 66° C. to 70° C. to obtain methyl (R)-2-(1,5,5-trimethylcyclopent-2-en-1-yl)acetate followed by adding lithium aluminium hydride (LAH) to a cold solution of compound of step (e) in tetrahydrofuran followed by stirring the reaction mixture for the time period ranging from 2 to 3 h at the temperature ranging from 25° C. to 30° C. to obtain (R)-2-(1,5,5-trimethylcyclopent-2-en-1-yl)ethan-1-ol ((−)-(7a);
f) stirring the reaction mixture of compound of step (f) in dichloromethane, triethylamine, acetic anhydride and 4-dimethylaminopyridine for the time period ranging from 3 to 4 h at the temperature ranging from 25° C. to 30° C. to obtain (R)-2-(1,5,5-trimethylcyclopent-2-en-1-yl)ethyl acetate.

5. The process as claimed in claim 1, for preparation of (R) and (S) enantiomers of sex pheromones of the long tailed mealybug said process consisting of steps:
wherein said process for preparation of (S)-(+)-pheromone consists comprising the steps of:
a) adding acetic acid, hydrogen peroxide and $H_2SO_4$ to (+)-5-oxobornylacetate and stirred for the time period ranging from 24 to 26 h at the temperature ranging from 25° C. to 30° C. followed by work up, removal of solvent and addition of potassium carbonate and further stirring for the time period ranging from 3 to 4 h to obtain (3aS,5S,6aR)-5-hydroxy-3a,4,4-trimethylhexahydro-2H-cyclopenta[b]furan-2-one ((+)-3);
b) adding pyridinium dichromate to a solution of compound of step (a) followed by stirring for the time period ranging from 8 to 10 h at the temperature ranging from 25° C. to 30° C. to obtain (3aS,6aR)-3a,4,4-trimethyltetrahydro-2H-cyclopenta[b]furan-2,5(3H)-dione ((+)-4);
c) refluxing the reaction mixture of p-toluene sulphonic acid and a solution of compound of step (b) in methanol for the time period ranging from 24 to 26 h at the temperature ranging from 65° C. to 70° C. to obtain methyl (S)-2-(1,5,5-trimethyl-4-oxocyclopent-2-en-1-yl)acetate ((+)-5);
d) adding Cerium(III) chloride heptahydrate and sodium borohydride to a cold solution of compound of step (c) in methanol followed by stirring the reaction mixture for the time period ranging from 1 to 2 h at the temperature ranging from 25° C. to 30° C. to obtain methyl 2-((1S)-4-hydroxy-1,5,5-trimethylcyclopent-2-en-1-yl)acetate (6');
e) adding boron trifluoride, diethyl etherate and sodiumcyanoborohydride to a cold solution of compound of step (d) in tetrahydrofuran followed by refluxing the reaction mixture for 8 to 10 hours at the temperature ranging from 66° C. to 70° C. to obtain methyl (S)-2-(1,5,5-trimethylcyclopent-2-en-1-yl)acetate followed by adding lithiumaluminiumhydride (LAH) to a cold solution of compound of step (e) in tetrahydrofuran followed by stirring the reaction mixture for the time period ranging from 2 to 3 h at the temperature ranging from 25° C. to 30° C. to obtain (S)-2-(1,5,5-trimethylcyclopent-2-en-1-yl)ethan-1-ol ((+)-(7a);
f) stirring the reaction mixture of compound of step (f) in dichloromethane, triethylamine, acetic anhydride and 4-Dimethylaminopyridine for the time period ranging from 3 to 4 h at the temperature ranging from 25° C. to 30° C. to obtain (S)-2-(1,5,5-trimethylcyclopent-2-en-1-yl)ethyl acetate.

6. Novel intermediates of process as claimed in claim 1, wherein the intermediates of said process are selected from (3aS,5S,6aR)-5-hydroxy-3a,4,4-trimethylhexahydro-2H-cyclopenta[b]furan-2-one, (3 aS,6aR)-3a,4,4-trimethyltetrahydro-2H-cyclopenta[b]furan-2,5(3H)-dione, methyl-2-(1,5,5-trimethyl-4-oxocyclopent-2-en-1-yl)acetate, methyl 2-((1R)-4-hydroxy-1,5,5-trimethylcyclopent-2-en-1-yl)acetate.

7. The process as claimed in claim 1, wherein said acylating agent is acetic anhydride in step (f).

8. The process as claimed in claim 1, wherein said base is triethylamine and catalyst is 4-dimethylaminopryridine in step (f).

9. The process as claimed in claim 1, wherein said base in step (a) is potassium carbonate.

* * * * *